(12) United States Patent
Liu et al.

(10) Patent No.: US 8,511,305 B2
(45) Date of Patent: Aug. 20, 2013

(54) REDUNDANT POWER CONTROL FOR RESPIRATORY SYSTEM HEATERS

(75) Inventors: Zhan Liu, Fremont, CA (US); Robert L. Snyder, Suwanee, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1365 days.

(21) Appl. No.: 11/927,054

(22) Filed: Oct. 29, 2007

(65) Prior Publication Data

US 2009/0107493 A1 Apr. 30, 2009

(51) Int. Cl.
*A62B 9/00* (2006.01)
*A61M 16/16* (2006.01)
*F24J 3/00* (2006.01)

(52) U.S. Cl.
CPC ............. *A62B 9/00* (2013.01); *A61M 16/16* (2013.01); *F24J 3/00* (2013.01)
USPC ........... 128/204.17; 128/202.22; 128/200.24; 128/204.18; 128/204.21

(58) Field of Classification Search
USPC ............ 128/200.24, 201.13, 204.18, 204.21, 128/203.12, 203.16, 203.17, 203.26, 203.27, 128/204.17; 239/338, 102.1, 102.2; 261/DIG. 65, 129, 154; 122/4 A, 5.5 A, 7 B, 13.01, 122/13.3–19.2, 33, 487, DIG. 7
See application file for complete search history.

(56) References Cited

U.S. PATENT DOCUMENTS

| | | | |
|---|---|---|---|
| 3,632,944 A * | 1/1972 | Lease | 219/624 |
| 3,987,133 A | 10/1976 | Andra | |
| 4,201,204 A * | 5/1980 | Rinne et al. | 128/203.27 |
| 4,291,838 A | 9/1981 | Williams | |
| 4,298,938 A | 11/1981 | Wang et al. | |
| 4,521,871 A | 6/1985 | Galdun et al. | |
| 4,682,010 A * | 7/1987 | Drapeau et al. | 392/488 |
| 4,708,831 A | 11/1987 | Elsworth et al. | |
| 4,903,191 A | 2/1990 | Fries | |

(Continued)

FOREIGN PATENT DOCUMENTS

| | | |
|---|---|---|
| GB | 2176405 A | 12/1986 |
| JP | H04-90033 | 3/1992 |
| JP | 2002142987 | 5/2002 |
| WO | 01/13981 | 3/2001 |

OTHER PUBLICATIONS

European Search Report in counterpart European Application No. 08 16 7314 (4 pages).

(Continued)

*Primary Examiner* — Annette Dixon
(74) *Attorney, Agent, or Firm* — Wood, Herron & Evans, LLP (57) ABSTRACT

A humidification system is provided for a respiratory system is provided with a controller having two processors that monitor the operation of each other and of heating elements in the respiratory system to provide CPU redundancy and heating element control. Each heating element is provided with two control paths, for example a relay and a triac connected in series with the heating element and a power supply. Each heater element has one control path connected to a first one of the processors and at least one heating element has at least one control path connected to a second one of the controllers. A hardware watchdog monitors the operation of the first processor, and can be triggered by a signal from the second processor, in response to which it can disable all heating elements.

17 Claims, 4 Drawing Sheets

(56) References Cited

U.S. PATENT DOCUMENTS

| | | | |
|---|---|---|---|
| 4,953,557 A | 9/1990 | Frankenreiter et al. | |
| 5,108,372 A | 4/1992 | Swenson | |
| 5,195,976 A | 3/1993 | Swenson | |
| 5,474,062 A | 12/1995 | DeVires et al. | |
| 5,494,028 A | 2/1996 | DeVries et al. | |
| 5,590,648 A | 1/1997 | Mitchell et al. | |
| 5,796,183 A | 8/1998 | Houmand | |
| 5,906,315 A | 5/1999 | Lewis et al. | |
| 5,943,473 A | 8/1999 | Levine | |
| 5,966,305 A | 10/1999 | Watari et al. | |
| 6,050,260 A * | 4/2000 | Daniell et al. | 128/204.22 |
| 6,061,601 A | 5/2000 | Jansen et al. | |
| 6,078,730 A | 6/2000 | Huddart et al. | |
| 6,349,722 B1 * | 2/2002 | Gradon et al. | 128/203.17 |
| 6,584,972 B2 * | 7/2003 | McPhee | 128/203.17 |
| 6,641,556 B1 | 11/2003 | Shigezawa | |
| 6,642,487 B2 * | 11/2003 | Stanzel | 219/494 |
| 6,694,974 B1 * | 2/2004 | George-Gradon et al. | 128/203.17 |
| 6,988,497 B2 | 1/2006 | Levine | |
| 7,140,367 B2 * | 11/2006 | White et al. | 128/204.17 |
| 7,722,016 B2 | 5/2010 | Bradley et al. | |
| 2003/0231116 A1 | 12/2003 | Jespersen et al. | |
| 2005/0051168 A1 | 3/2005 | DeVries et al. | |
| 2005/0124866 A1 | 6/2005 | Elaz et al. | |
| 2005/0133027 A1 | 6/2005 | Elaz et al. | |
| 2005/0143632 A1 | 6/2005 | Elaz et al. | |
| 2008/0054497 A1 | 3/2008 | Bradley et al. | |
| 2008/0054500 A1 | 3/2008 | Bradley et al. | |
| 2009/0107496 A1 | 4/2009 | McGhin et al. | |
| 2009/0107980 A1 | 4/2009 | Andel et al. | |
| 2009/0107982 A1 | 4/2009 | McGhin et al. | |
| 2009/0110022 A1 | 4/2009 | Snyder et al. | |
| 2009/0110029 A1 | 4/2009 | Bradley et al. | |
| 2009/0110378 A1 | 4/2009 | Bradley et al. | |
| 2009/0110379 A1 | 4/2009 | McGhin et al. | |

OTHER PUBLICATIONS

Manual for Fisher & Paykel Model Nos. MR700, MR720, MR730 Respiratory Humidifiers (Mar. 1998) (48 pages).

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Brochure for Hudson RCI Humid-Heat® (6 pages).

Operating Manual for Fisher & Paykel Model Nos. MR700, MR720, MR730 Respiratory Humidifiers (Mar. 1994) (46 pages).

Instruction Sheet for Airlife® Single Heated Adult Respiratory Circuit (2 pages) (date uncertain).

Cardinal Health RT110 Data for Circuits, reprinted from the internet Jun. 3, 2006 (2 pages).

Fisher & Paykel 900MR561 Temperature Probe Label (one page) (date uncertain).

Fisher & Paykel Airway Temperature Probes Instructions for Use (3 pages) (2003).

Cat. RT110 Insert for Airlife™ Adult Respiratory Circuit—Heated (one page) (undated).

Official Action issued in corresponding Japanese Patent Application No. 2008-277051, dated Jan. 8, 2013, and English translation thereof (6 pages).

* cited by examiner

REDUNDANT POWER CONTROL FOR RESPIRATORY SYSTEM HEATERS

FIELD OF THE INVENTION

The present invention relates to power control of respiratory system heaters.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit of a breathing circuit. The breathing circuit may also include expiratory limb hose or conduit to carry expelled air and other gas(es) from the patient back to the ventilator or to atmosphere.

It is typically desired to warm and impart humidity to the breathable gas before it is provided to the patient. For that purpose, many respiratory systems include a humidification system having a heater unit and a disposable water chamber adapted to be heated by the heater unit. The heater unit supports a heater, such as a hot plate heater which may be comprised of one or more heating elements and a metal plate defining a hot plate. A wall of the chamber, such as the bottom surface thereof, is thermally conductive. The chamber is removably supported on the heater unit with the bottom surface in thermal contact with the hot plate of the heater unit to thus heat the water in the chamber. The chamber may be manually refillable, or there may be a water source to selectively fill the chamber as it empties. The breathable gas is coupled to the chamber and is passed through the chamber to be heated and humidified. Examples of heater units, chambers and vented water supplies are shown in U.S. Pat. Nos. 7,722,016, 6,988,497, and 5,943,473; and U.S. Patent Publication No. 2008/0054497.

The inspiratory limb carries the heated and humidified gas to the patient and the expiratory limb, if present, carries exhaled air and possibly other gases from the patient. The hoses or conduits of the inspiratory and expiratory limbs may each be provided with a heater, referred to as a heater circuit, to add heat to the gas passing through the limb and to avoid the incidence of potentially dangerous or hazardous rainout of condensation from the gas(es) passing through the limb. The heater circuit may be in the form of one or more elongated, and possibly coiled, heater wires running along the limb, such as through the interior of the limb. An example of a breathing circuit with heated limbs is shown in U.S. Pat. No. 6,078,730. The heater unit typically houses the necessary electrical and electronic components to regulate the temperature of the hot plate, as well as heating circuits of the inspiratory and/or expiratory limbs of the breathing circuit.

Regulating the temperature of those heaters can be essential to proper operation of the respiratory system. By way of example, a single point of failure in the control path for the heater, such as in the hardware or software of the electronic components in the heater unit, could lead to undesirable overheating of the hot plate or one of the heater circuits in the breathing circuit. Depending on the level of overheating, the consequences can be quite serious. While some level of protection is obtained with safety cut-offs, such as in the form of a fuse or thermal breaker or the like, additional levels of control are desirable to reduce the risk of overheating from a single point of failure.

SUMMARY OF THE INVENTION

The present invention provides an electronic control path with features to reduce the risk of overheating from a single point of failure. To that end, and in accordance with the principles of the present invention, dual central processing unit (CPU) redundancy, dual control paths, hardware CPU monitoring overrides, or combinations thereof are provided to control the heaters.

According to certain principles of the invention, a humidification system may be provided with a heating control having two separate control paths from a CPU. The paths may include the same or different types of devices, such as, for example, relays, gated triacs or other solid state switching devices, or other types of switching devices.

According to an illustrated embodiment of the invention, the control of each of a plurality of heaters includes a triac which provides independent control of the amount of the power to the respective heater, as well as shutoff of that power, plus a separate safety shutoff relay to interrupt power through the respective triac.

Further according to principles of the present invention, each heating element is energized by at least two of a plurality of switching devices being in a conductive state, the conductive states being controlled by at least two processors or CPUs.

According to one embodiment of the invention, a humidification system may be provided with more than one CPU, for example a main CPU and an auxiliary CPU, each of which can disable any of a plurality of heating elements. According to certain embodiments of the invention, each CPU can monitor one or more heating elements and can monitor one or more other CPUs. According to other embodiments of the invention, a hardware watchdog is provided that can be configured to monitor a CPU, for example the main CPU, or to be gated off by a CPU, for example by the auxiliary CPU, or to disable any heating element, or to disable all heating elements, or perform any combination of these functions.

While the present invention is primarily directed towards heated humidifier systems, other uses and applications will become apparent to those skilled in the art.

These and other objectives and advantages of the present invention will be more readily apparent from the following detailed description of the drawings.

BRIEF DESCRIPTION OF THE DRAWINGS

The accompanying drawings, which are incorporated in and constitute a part of this Specification, illustrate an embodiment of the invention and, together with the general description of the invention given above and the detailed description of the embodiment given below, serve to explain the principles of the present invention.

DETAILED DESCRIPTION OF THE DRAWINGS

Figure 1:
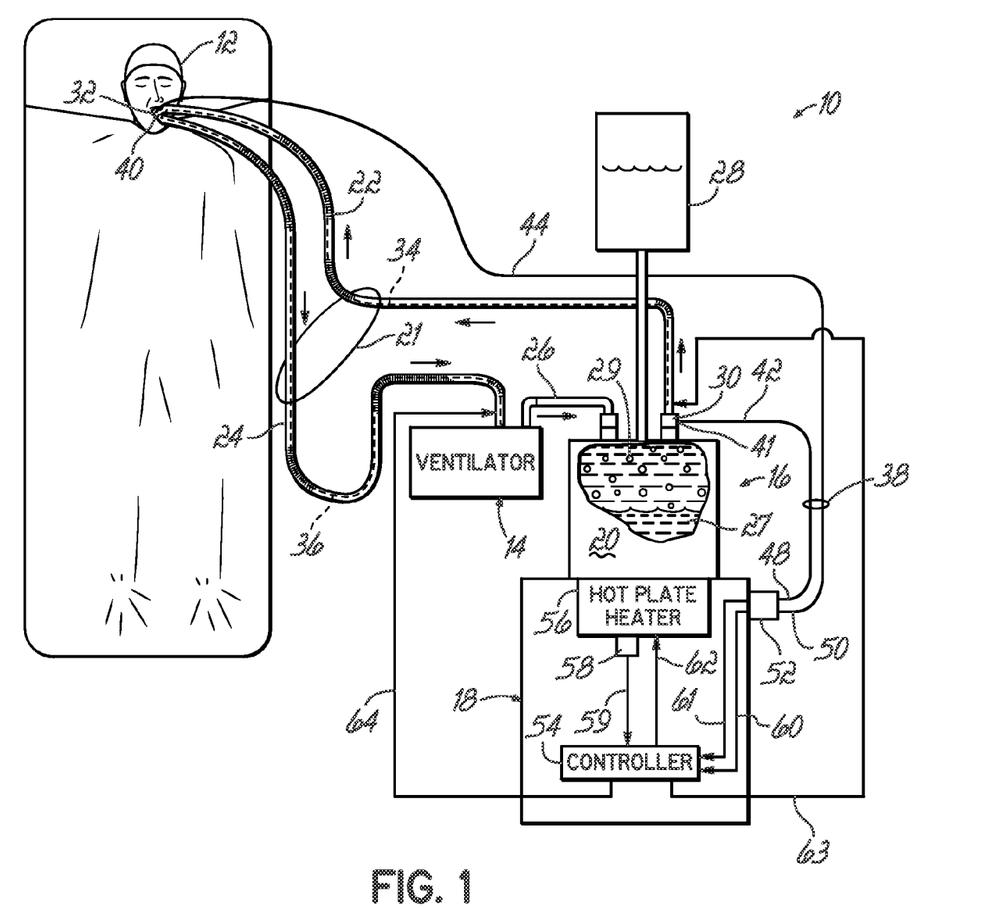
FIG. 1 is a diagram of a respiratory system having a heater unit adapted with features constructed in accordance with the principles of the present invention.

FIG. 1 is an exemplary respiratory system 10 for supplying breathable gases to a patient 12. In the illustrated embodiment, the respiratory system 10 includes a ventilator 14, a humidification system 16 having a heater unit 18, a heatable container for water such as a disposable chamber 20, and a breathing circuit 21 having a first elongated hose or conduit defining an inspiratory limb 22 and a second elongated hose or conduit defining an expiratory limb 24. Ventilator 14 drives breathable gas, such as oxygen, anesthetic gas and/or air, through gas conduit 26 and into an air inlet of chamber 20. Water 27 is received in chamber 20, either by being poured in manually or automatically from a water supply 28 such as a bag or bottle, and which may be vented. Chamber 20 is heated by heater unit 18 to heat up the water 27 therein. Heated water vapor 29 may also be produced within chamber 20 above the level of water 27 therein. The gas from conduit 26 passes over or through the heated water 27 and/or through heated water vapor 29 to become heated and humidified before exiting the chamber 20 as heated and humidified gas.

The heated and humidified gas flows from chamber 20 to the patient 12 by passing through inspiratory limb 22. A first end of inspiratory limb 22 is coupled to chamber 20 by a connecting member or joint 30, and a second end of inspiratory limb 22 is coupled to a breathing attachment 32 that facilitates delivery of the gas passed therethrough to the patient 12. The breathing attachment 32 may couple to an invasive apparatus such as an endotracheal tube, or a non-invasive apparatus such as a mask (both not shown) that promotes gas delivery. The gas may be further heated while passing through inspiratory limb 22 to breathing attachment 32 by a heater 34, referred to as a heater circuit, associated with inspiratory limb 22. Expiratory limb 24 allows exhaled air and other gas expelled from patient 12 to pass back to ventilator 14. Another heater 36, also referred to as a heater circuit, is associated with expiratory limb 24 for heating the expelled gas. Heater circuits 34 and 36 may be comprised of one or more elongated, coiled heater wires extending along or through limbs 22 and 24, respectively, although different types of heater circuits or wire configurations could be employed.

Respiratory system 10 may also includes a patient temperature cable (PTC) 38 having one or more temperature responsive devices such as thermistor-containing probes 40, 41 to provide thermal feedback in the form of temperature readings to heater unit 18 for purposes to be described. Temperature cable 38 includes a first communication cable 42 and a second communication cable 44. Temperature probe 41 is coupled to joint 30 at the entry to inspiratory limb 22 to provide a temperature reading via first communication cable 42 indicative of the actual measured temperature of the heated and humidified gas exiting from chamber 20 ("the output temperature"). Temperature probe 40 is coupled to breathing attachment 32 at the exit of inspiratory limb 22 to provide a temperature reading via second communication cable 44 indicative of the actual measured temperature of the humidified gas being provided to the patient ("the patient temperature"). First communication cable 42 has an end 48 electrically coupled to heater unit 18 to communicate the output temperature to heater unit 18. Similarly, second communication cable 44 has an end 50 electrically coupled to heater unit 18 to communicate the patient temperature to heater unit 18. Ends 48 and 50 may be advantageously secured together through a connector 52 to facilitate coupling the first and second cables 42, 44 to a mating socket (not shown) on heater unit 18. Further details of a suitable cable 38 and probes 40 or 41 are set out in U.S. Patent Publication Nos. 2009/0110029 and 2009/0110378, the disclosures of both of which are incorporated herein in their entirety by reference.

Heater unit 18 includes a controller 54 and a heater 56 in the form of a hot plate heater. An example of one suitable heater 56 is described in concurrently filed U.S. Patent Publication No. 2009/0107980, the disclosure of which is incorporated herein by reference in its entirety. Thermally coupled to heater 56 is a temperature responsive device such as a thermistor 58 to provide readings of the measured temperature of the hot plate (not shown) of heater 56 to controller 54 ("the input temperature"). The input temperature is representative of the heat input to the chamber 20, and is coupled to controller 54 as at 59. The patient and output temperature readings are also coupled to controller 54 as at 60 and 61, respectively. The various temperature readings are utilized by controller 54 to control the functions of heater unit 18, including regulating the temperature of heater 56 and heater circuits 34, 36, such as with power signals as at 62 for heater 56 and as at 63 and 64 for heater circuits 34, 36, respectively.

Figure 2:
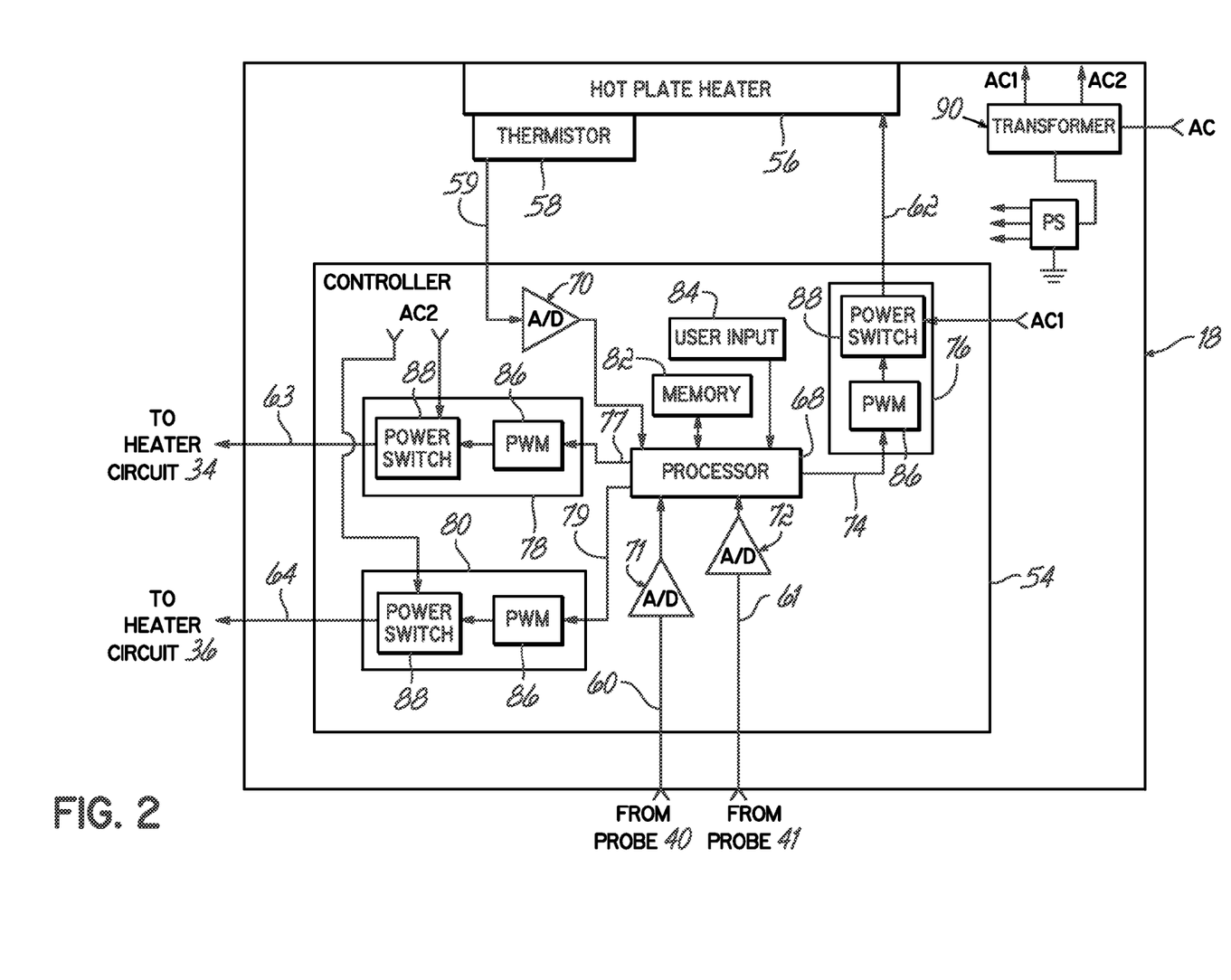
FIG. 2 is a schematic diagram of the heater unit of FIG. 1 having a controller incorporating the features.

As seen in greater detail in FIG. 2, controller 54 includes a processor 68 operatively associated with probes 40 and 41, temperature responsive device 58, heater 56, and heater circuits 34 and 36. The input temperature readings from temperature responsive device 58 are communicated to processor 68 as at 59 via A/D converter 70. The patient temperature readings from probe 40 are communicated to processor 68 as at 60 via A/D converter 71. The output temperature readings from probe 41 are communicated to processor 68 as at 61 via A/D converter 72. Controller 54 could also include an amplifier with an adjustable offset and with processor 68 adapted to determine the offset and have an adjustable scaling factor as described in U.S. Patent Publication No. 2009/0110022, the disclosure of which is incorporated herein by reference in its entirety. Processor 68 outputs a heater control signal as at 74 to control a power circuit 74 to selectively electrically energize heater 56, as at 62, for regulating the temperature thereof so as to control heating of water 27 in chamber 20. If a heated breathing circuit 21 is present, processor 68 is also adapted to control heating of heater circuits 34 and 36. To that end, processor 68 outputs an inspiratory control signal as at 77 to control a power circuit 78 to selectively electrically energize heating circuit 34, as at 63 for regulating the heat input to gas passing through inspiratory limb 22 and/or processor 68 outputs an expiratory control signal as at 79 to control a power circuit 80 to selectively electrically energize heating circuit 36, as at 64, for regulating the heat input to gas(es) passing through expiratory limb 24. Processor 68 operates under programs or algorithms stored in a memory 82 and in response to data input via a user input 84. Presence of a heated breathing circuit 21 may be indicated via the user input 84 or may be automatically detected as described in U.S. Patent Publication No. 2009/0107982, the disclosure of which is incorporated herein by reference in its entirety. Processor 68 advantageously utilizes PID feedback control for generating the heater, inspiratory and expiratory control signals as described in U.S. Patent Publication No. 2009/0110379, the disclosure of which is also incorporated herein by reference in its entirety.

Each power control circuit includes a control circuit such as a pulse width modulator ("PWM") circuit 86 and a power switch 88, such as a gated triac or the like, so as to regulate the amount of AC power coupled therethrough, such as from one or more taps AC1 and AC2 of a transformer 90 in relation to the control signal (74, 77 or 79) whereby to selectively electrically energize the respective heater 56, heater circuit 34 or heater circuit 36. PWM circuit 86 may modulate power switch 88 either by turning it on and off or by varying its conductance as desired whereby to provide the desired selective energization in a manner intended to desirably heat and humidify gas passing through chamber 20 and/or limbs 22 and 24. Signals 74, 77 and 79 can each be independently developed by processor 68, and operable for managing separate power circuits 76, 78 and 80 as described in the aforesaid U.S. Patent Publication No. 2009/0110379 and in U.S. Patent Publication No. 2009/0107496, the disclosure of which is also incorporated herein by reference in its entirety. Heater unit 18 may include a power supply (PS) coupled to transformer 90 to provide one or more regulated DC voltage levels for use in powering the various aspects of controller 54. Heater unit 18 may also include one or more displays, input controls such as buttons and dials or the like (an example of which is user input 84), and alarm indicators (all otherwise not shown), and may further have various interface inputs and outputs such as to couple to a source of AC power and to the heater circuits 34, 36, and PTC cable 38. As will be appreciated, while the various devices of controller 54 are shown as being separately coupled to processor 68, they may communicate over one or more common busses. Also, one or more of power switches 88 may be mounted on heat sinks or the like (not shown) separate from the rest of the circuitry of controller 54. Power for heater 56 is shown as being via tap AC1 of transformer 90, but it will be appreciated that heater 56 could alternatively be powered via the source of AC used to power transformer 90.

The architecture of the control of heater unit 18 in the illustrated embodiment of the invention primarily protects against single point failures that would have power delivered to hotplate heater 56 and heater circuits 34, 36 under conditions that could be unsafe or are otherwise undesirable. In order to reduce the risk of single point failure, redundancy of the control paths such as for the AC power to control switches 88 is provided in accordance with the principles of the present invention.

Figure 3:
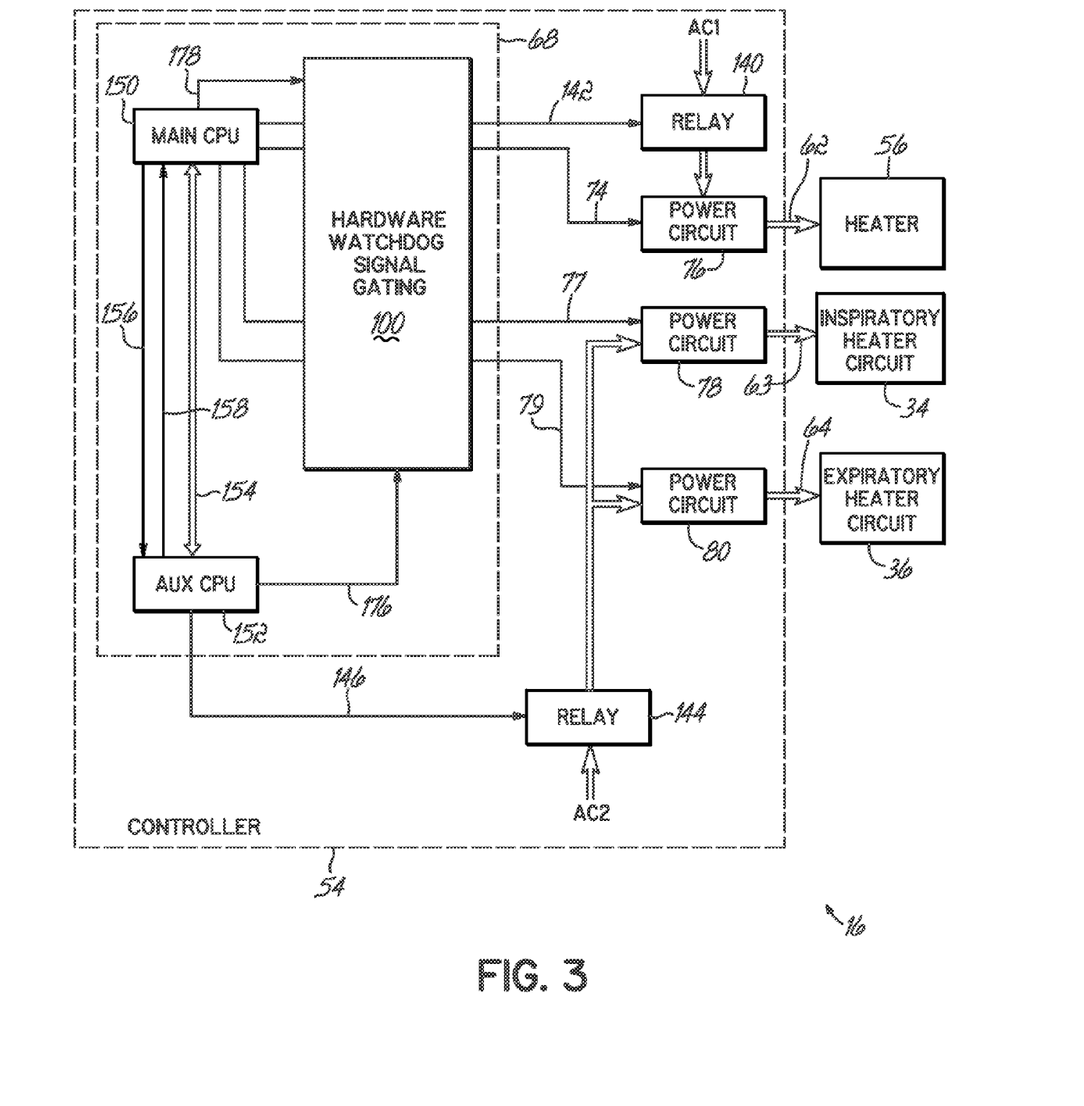
FIG. 3 is a block diagram of the controller of FIG. 2 coupled to heaters of the system of FIG. 1 for purposes of explaining the principles of the present invention.

By way of example, and with particular reference to FIG. 3, a relay 140, which may be a normally-open relay, is electrically coupled in series between the AC power tap AC1 (or source AC) and power circuit 76 for heater 56 so as to normally interrupt or cut-off power to heater 56. Relay 140 is responsive to a power signal as at 142 from processor 68 by which to close relay 140 and thus provide power for heater 56. The electrical voltage or current that is passed through relay 140 is gated by power circuit 76. Termination of power signal 142 causes relay 140 to re-open thus cutting off power to heater 56. Hence, processor 68 not only controls selective energization of heater 56 via power circuit 76, but additionally controls coupling of power to power switch 88 of power circuit 76 so as to provide a redundant level of control by which to shut off power to heater 56 if desired or necessary. As a consequence, heater 56 will not receive power and thus cannot be heated, except during those times that both relay 140 and power switch 88 of power circuit 76 are both closed, i.e., both must be in a conductive state. Alternatively, relay 140 may be a normally-closed relay so as to normally provide power to power circuit 76 and will open to cut-off power in response to a power signal as at 142 from processor 68.

Heated wire power output AC2 from transformer 90 is a low voltage AC output of, for example, 22 VAC, and provides electrical power to inspiratory heater circuit 34 and if provided, expiratory heater circuit 36. Single point failure protection is further manifested, in part, by delivering this power through a relay 144, which is connected in series with each of the power circuits 78 and 80 to the respective heater circuits 34, 36. The electrical voltage or current that is passed through relay 144 is gated by power circuits 78, 80. Relay 144, which may be a normally-closed relay so as to normally provide power to heater circuits 34 and 36 may open in response to a power signal as at 146 from processor 68. Termination of power signal 146 causes relay 144 to re-close thus providing power again to heater circuits 34 and 36. Hence, processor 68 not only controls selective energization of heater circuits 34 and 36 via power circuits 78 and 80, respectively, but additionally controls coupling of power to power switches 88 of heater circuits 34 and 36 so as to provide a redundant level of control by which to shut off power to heater circuits 34 and 36 if desired or necessary. As a consequence, heater circuits 34 and 36 will not receive power and thus cannot be heated, except during those times that both relay 144 and respective power switch 88 of power circuit 78 and/or 80 are both closed, i.e., both must be in a conductive state. Alternatively, relay 144 may be a normally-open rely that is responsive to a power signal as at 146 from processor 68 by which to close relay 144 and thus provide power for heater circuits 34, 36. By requiring both a control signal and a power signal to energize a heater, a single point of failure in the power control pathways for a heater is avoided.

Processor 68 may be a single microprocessor or other computer or programmable logic device. Advantageously, however, processor 68 may be defined by redundant CPUs in order to provide even greater control over power to the heaters and thus further points in the control pathways so as to avoid the consequences of a single point of failure. To that end, processor 68 may include a main CPU 150 and an auxiliary CPU 152 which communicate through a CPU serial peripheral interface 154 and inter-processing timing signals 156 and 158.

Main CPU 150 is adapted to handle user interface tasks, temperature measurement, communication and debugging capabilities, control of heater 56 as above-described, and initialization of alarms. Main CPU may also handle calibration of temperature measurement circuitry as described in aforementioned U.S. Patent Publication No. 2009/0110022. Auxiliary CPU 152 is adapted to handle responsibilities such as verifying that the proper heated hose wire is being used as described in aforementioned U.S. Patent Publication No. 2009/0107982.

Main CPU 150 generates control signals 74 by which to regulate the temperature of heater 56 so as to heat water 27 in chamber 20. Main CPU 150 also generates control signals 77 and 79 by which to regulate the temperature of heater circuits 34 and 36 in limbs 22 and 24 of breathing circuit 21. Main CPU is also adapted to provide power signal 142 for control of relay 140.

Main CPU 150 monitors feedback from the system, such as the temperature readings and other signals. For example, main CPU 150 monitors the proper control of heater 56 by the temperature readings from probe 40 and/or probe 41, i.e., at 60 and/or 61, respectively. Additionally, the monitoring of proper control of heater circuits 34, 36 is performed by the main CPU 150. Main CPU 150 also controls power to heater circuits 34, 36 by turning power on and off during a specific time window, e.g., a 2 second window. Main CPU 150 also monitors the temperature reading from thermistor 58 as at 59 to provide additional heater performance data, to prevent, for example, heater 56 from operating at excessive temperatures. Alarm conditions will result for high and low patient airway temperature and high and low water-chamber temperature.

Alternatively, auxiliary CPU 152 could also monitor temperature readings to provide redundant monitoring of the performance of heater 56 and heater circuits 34, 36. For example, auxiliary CPU 152 could monitor proper control of inspiratory heater circuit 34 independent of main CPU 150 by monitoring the control signals from the main CPU 150. If main CPU 150 issues a command to energize or de-energize inspiratory heater circuit 34, and that action is not accomplished, a high priority alarm would be generated. Similarly, auxiliary CPU 152 could generate a high priority alarm if other abnormal conditions in the operation of main CPU 150 were detected, such as the power circuit 78 (or power circuit 80) always being in a logic on state, i.e., inspiratory heater circuit 34 (or expiratory heater circuit 36) is always being energized. Finally, auxiliary CPU 152 is adapted to provide power signal 146 for relay 144. In other words, relay 144 is controlled directly by output 146 from auxiliary CPU 152.

Each CPU 150, 152 can disable heater 56 or heater circuit 34, 36, by either direct control, by controlling a hardware watchdog module 100, or by communicating with the other CPU through communication path 154. Further, each CPU 150, 152 monitors a timing signal from the other CPU 152, 150 to confirm timebase match. For each CPU 150, 152 to communicate with the other, each CPU 150, 152 must be in logical program execution, and when communication with the other CPU is lost, the response of each CPU is to disable or de-energize all heating elements with a gating function, i.e., a discrete logic circuit, including, for example, hotplate heater 56 of heater unit 18 and heater circuits 34, 36 of breathing circuit 21.

Hardware watchdog module 100 and CPUs 150 and 152 provide a number of watchdog functions, including a software watchdog function, an inter-microcontroller watchdog function, and a heater watchdog function. The software watchdog function is implemented in main CPU 150 and auxiliary CPU 152. The software watchdog function's purpose is to be sure that all status flags in the main loop are received before main CPU 150 or auxiliary CPU 152 timers expire. Failure to execute code in the main loop of CPUs 150, 152 in a specified time causes a high priority alarm condition. In other words, the software watchdog will detect the execution of erroneous timing instructions or deviations by either CPU 150, 152.

The software watchdog function, which is performed in CPUs 150, 152, executes off of a timer interrupt at regular intervals, for example every 100 ms, and runs through logic to assure that the program loop of CPUs 150, 152 all real-time tasks are running. This software watchdog function uses flags stored in shared memory that are cleared by the real-time tasks and main program loop each time the respective code executes. The flags are reset by the software watchdog. Each period executed by the software watchdog is the period during which all tasks and CPUs 150, 152 program loops must clear their respective flags. After this window expires, the software watchdog will check the flags to determine if the software is still executing as expected. If so, the software watchdog resets. Otherwise, the software watchdog can be set in each CPU 150, 152 to shut down heater 56 and heater circuits 34, 36. Main CPU 150 de-energizes the heater 56 and heater circuits 34, 36 by opening power switches 88, i.e., by not providing a signal that would turn the triac(s) on and/or by providing a signal that opens them, and/or by stopping timing pulses to the watchdog 100 which will also open or not energize power switches 88. Main CPU 150 also de-energizes heating element 56 by deactivating, i.e., opening relay 140. Auxiliary CPU 152 can de-energize heater 56 and heater circuits 34, 36 by sending a signal to the watchdog module 100. As such, the software watchdog monitors CPUs 150, 152 for proper operation.

Figure 4:
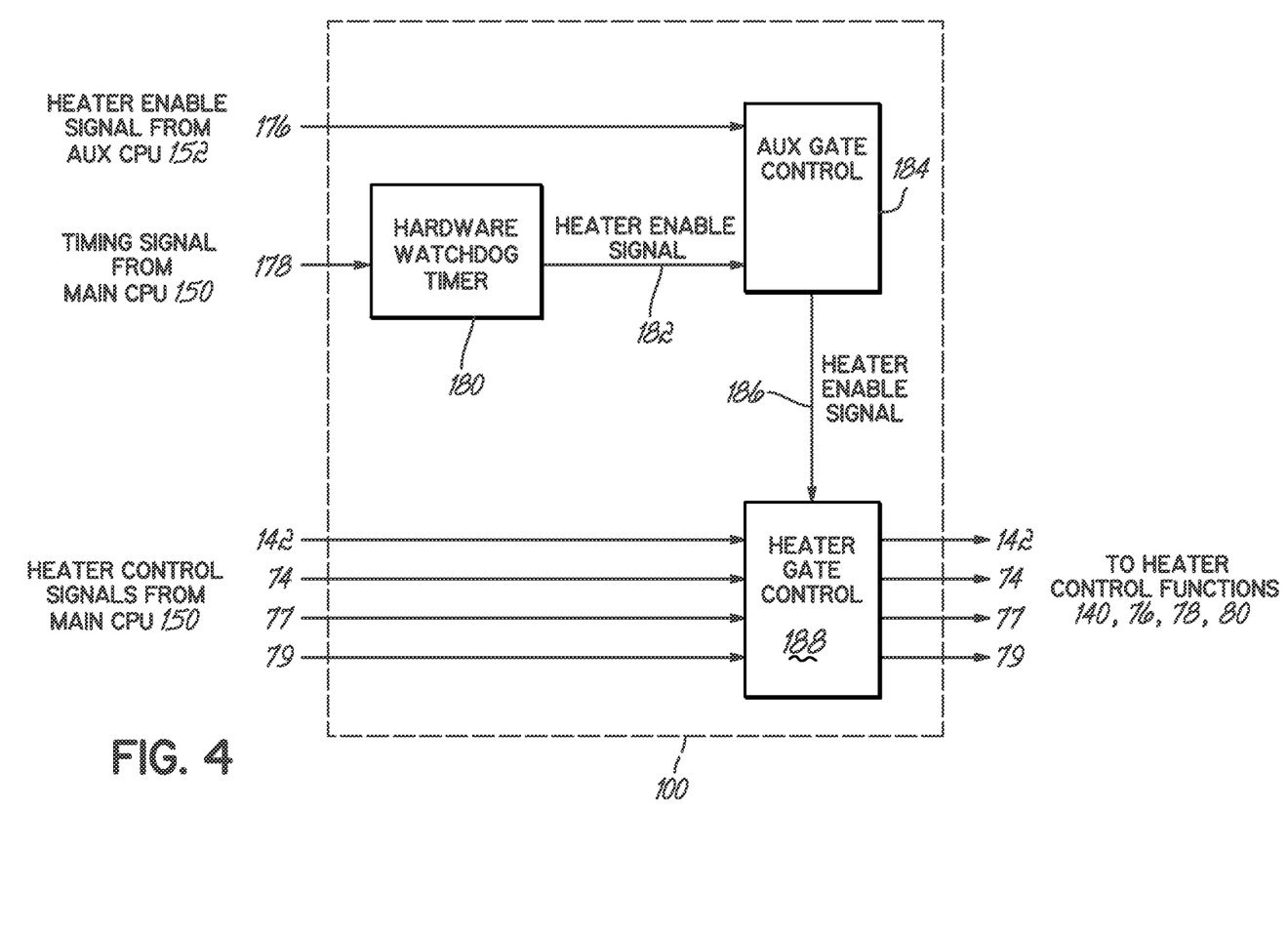
FIG. 4 is a block diagram of the watchdog module of the controller of FIG. 3.

With reference to FIG. 4, watchdog module 100 may include a gating function, i.e., a logic circuit, which upon receipt of signal 176 from auxiliary CPU 152 will open power switches 88 (preventing power from reaching all heaters), and deactivating relay 140 to prevent power from reaching power circuit 76. More specifically, CPU 152 sends signal 176 to auxiliary gate control 184 in watchdog module 100. Auxiliary gate control 184 will in turn send an "OFF" heater enable signal 186 to a heater gate control 188. Heater gate control 188 will in turn either interrupt signals 74, 77, 79 to cause power switches 88 not to energize, or will introduce substitute signals at 74, 77, 79 to turn off power switches 88, either of which will prevent power from reaching power circuits 76, 78, 80, thus disabling heaters 56, 34 and 36. Heater gate control 188 will also terminate the power signal 142 to open relay 140 and de-energize power circuit 76 to redundantly disable heater 56. Auxiliary CPU 152 can also activate relay 144 to prevent power from reaching power circuits 78, 80.

The inter-microcontroller watchdog function's purpose is to test the relative time base of each CPU 150, 152. This is accomplished by each processor monitoring a timing signal 156, 158 from the other processor. By way of example, each CPU sends a series of pulses to the other CPU which are in turn counted in a time window. If the requisite number of pulses are not received, a high priority alarm condition results.

In operation, auxiliary CPU 152 outputs a timing signal 158, for example, at a 2 Hz rate, that is monitored by main CPU 150. Main CPU 150 can monitor this timing signal 158 over an interval of, for example, 1.5 seconds, and can test for the presence of 2 to 4 pulses in that window. If main CPU 150 does not detect this expected number of pulses, it can turn off heater 56 and heater circuits 34, 36 by issuing a command to open power switches 88, thus preventing power from reaching power circuits 76, 78, 80. Additionally, main CPU 150 can terminate power signal as at 142 to open relay 140 to also prevent power from reaching power circuit 76. Main CPU 150 can also send a message to auxiliary CPU 152 to send a power signal as at 146 to open relay 144 to also prevent power from reaching power circuits 78, 80.

Similarly, main CPU 150 can output a timing signal 156, for example at a 5 Hz rate, that can be monitored by auxiliary CPU 152 over a window of, for example, 4 seconds in which it might text for the presence of from 19 to 21 pulses. If this expected number of pulses is not counted within the window, auxiliary CPU 152 can send a power signal as at 146 to open relay 144 to also prevent power from reaching power circuits 78, 80. Auxiliary CPU 152 can also send a signal to watchdog module 100 to terminate the power signal as at 142 to open relay 140 and de-energize power circuit 76. Finally, auxiliary CPU 152 can send a signal to watchdog module 100 to open power switches 88 (see FIG. 2) to de-energize all the power circuits 76, 78, 80. Auxiliary CPU 152 can also send an error code to be displayed, and update a frequency error code in an error status register so that main CPU 150 can read the error if it is able.

The heater watchdog also functions to monitor a main CPU 150 timing signal 178 and to disable or turn off heater 56 and heater circuits 34, 36 if timing signal 178 from main CPU 150 is not present in a requisite time window. By way of example, this could be accomplished by maintaining a logic level through charging a capacitor or by a digital timer function. In operation, main CPU 150 outputs timing signal 178 that is monitored by hardware watchdog timer 180 (FIG. 4) in watchdog module 100 for timing integrity. Should the signal 178 be absent or significantly slowed down, the heater watchdog function will time out and disable heater 56 and heater circuits 34, 36. For example, if signal 178 stays high or low for too long of a period of time, then watchdog timer 180 will output or keep heater enable signal 182 at a low logic voltage level, i.e, an "OFF" level. An auxiliary gate control 184 will in turn send an "OFF" heater enable signal 186 to a heater gate control 188 to thus shut down power to power circuits 76, 78, 80, and to terminate the power signal 142 to open relay 140 and de-energize power circuit 76 to thus disable heaters 56, 34 and 36, as previously described.

The heater watchdog function will also allow auxiliary CPU 152 to disable or turn off heater 56 and heater circuits 34, 36 even if signal 178 from main CPU 150 is not absent or significantly slowed down. In other words, if auxiliary CPU 152 detects an abnormality in the system, for example it does not receive a proper timing signal 156 from main CPU 150 or detects an error in the communication with main CPU 150 through CPU serial peripheral interface 154, auxiliary CPU 152 will output a logic signal 176 to the watchdog module 100. If CPU 150 detects a high priority alarm condition, it may also issue a command to auxiliary CPU 152 to also output a logic zero or "OFF" signal 176 to auxiliary gate control 184 in the watchdog module 100. Additionally, if the software watchdog function in auxiliary CPU 152 should detect an error condition, auxiliary CPU 152 will output logic "OFF" signal 176 to auxiliary gate control 184 in watchdog module 100. Auxiliary gate control 184 will in turn send an "OFF" heater enable signal 186 to a heater gate control 188 to thus disable heaters 56, 34 and 36 as described above.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. A humidifier system comprising:
    a heating element;
    a first power switch which turns on or off in response to a first control signal and a second power switch which turns on or off in response to a second control signal, the first and second power switches being in electrical series between a source of power and the heating element and both being required to be on for activation of the heating element;
    first and second processors, the first control signal being originated by the first processor and being provided therefrom to the first power switch along a first control path and the second control signal being originated by the second processor and being provided therefrom to the second power switch along a second control path; and
    a watchdog being in the first control path in electrical series between the first processor and the first power switch, the watchdog operable to normally gate the first control signal from the first processor to the first power switch and to monitor at least one of the first and second processors, and the watchdog further operable to interrupt the first control signal from the first processor to the first power switch so as to disable the heating element in response to the monitoring of the at least one of the first and second processors.

2. The system of claim 1 wherein:
    one of the first and second power switches comprises a relay and the other of the first and second power switches comprises a solid state switching element.

3. The system of claim 2, wherein the solid state switching element is a triac.

4. The system of claim 1 wherein:
    each of the first and second processors is programmed to monitor a timing signal from the other processor and to disable the heating element in response to a detected failure of one of the timing signals.

5. The system of claim 1, wherein the watchdog is operable to monitor the first processor and to disable the heating element in response to the monitoring of the first processor.

6. A respiratory system comprising a humidifier system having:
    a heating element;
    a first power switch which turns on or off in response to a first control signal and a second power switch which turns on or off in response to a second control signal, the first and second power switches being in electrical series between a source of power and the heating element and both being required to be on for activation of the heating element;
    first and second processors, the first processor providing the first control signal to the first power switch along a first control path and one of the processors providing the second control signal to the second power switch along a second control path; and
    a watchdog being in the first control path in electrical series between the first processor and the first power switch, the watchdog operable to normally gate the first control signal from the first processor to the first power switch and to monitor at least one of the processors, and the watchdog further operable to interrupt the first control signal from the first processor to the first power switch so as to disable the heating element in response to the monitoring of the at least one processor, wherein:
    the first and second processors include a main processor and an auxiliary processor;
    the heating element includes a hotplate heater; and
    the respiratory system includes an inspiratory conduit and an expiratory conduit, each conduit connected to the humidification system and each having a heating element therein having a control having two control paths thereto, one responsive to a control signal from the main processor and the other responsive to a control signal from the auxiliary processor.

7. The respiratory system of claim 6 wherein:
    the watchdog is operable to monitor the main processor and to disable the heating elements in response to the monitoring of the main processor, the watchdog having an override responsive to the auxiliary processor and operable to disable the heating elements in response to a signal from the auxiliary processor.

8. A humidifier system controller for use in a respiratory system having a heating element, the controller comprising:
    a first CPU and a second CPU;
    a first set of switching devices comprising a first switching device responsive to a control signal from the first CPU and a second switching device responsive to a control signal from one of the first and second CPUs;
    conductors for connecting the heating element to a power supply through the two switching devices so as to energize the heating element in response to both of the two switching devices being in a conductive state;
    a hardware monitoring override operable to monitor the first CPU and to interrupt at least one of the first and second control signals, the first and second switching devices being responsive to the hardware monitoring override;

a second set of switching devices comprising two switching devices;
conductors for connecting a second heating element to the power supply through the two switching devices of the second set so as to energize the second heating element in response to both of the two switching devices of the second set being in a conductive state;
the second CPU providing a control signal to at least one switching device of the second set; and
the first CPU providing a control signal to both of the two switching devices of the second set.

9. The humidifier system controller of claim 8 wherein:
each of the two CPUs is programmed to monitor a timing signal from the other CPU over an interval, and to disable all heating elements in the respiratory system if the monitored timing signals are not as expected over the interval.

10. A humidifier system comprising:
a heating element;
a first power switch which turns on or off in response to a first control signal and a second power switch which turns on or off in response to a second control signal, the first and second power switches being in electrical series between a source of power and the heating element and both being required to be on for activation of the heating element;
first and second processors, the first processor providing the first control signal to the first power switch along a first control path and one of the processors providing the second control signal to the second power switch along a second control path; and
a watchdog being in the first control path in electrical series between the first processor and the first power switch, the watchdog operable to normally gate the first control signal from the first processor to the first power switch and to monitor at least one of the processors, and the watchdog further operable to interrupt the first control signal from the first processor to the first power switch so as to disable the heating element in response to the monitoring of the at least one processor, wherein the first processor is a main processor and the second processor is an auxiliary processor, and wherein the main processor provides the second control signal to the second power switch along the second control path, and wherein:
the heating element is a first heating element; and
the system further comprises
a second heating element, and
a third power switch which turns on or off in response to a third control signal and a fourth power switch which turns on or off in response to a fourth control signal, the third and fourth power switches being in electrical series between a source of power and the second heating element and both being required to be on for activation of the second heating element.

11. The system of claim 10 wherein:
the auxiliary processor is configured to activate the watchdog to disable the first and second heating elements.

12. The system of claim 11 wherein:
the first heating element is a respiratory humidifier heater;
the main processor provides the first, second, and third control signals;
the watchdog gates the first, second, and third control signals;
the second heating element is a respiratory conduit heater element; and
the auxiliary processor provides the fourth control signal.

13. A humidifier system comprising:
a heating element;
a first power switch which turns on or off in response to a first control signal and a second power switch which turns on or off in response to a second control signal, the first and second power switches being in electrical series between a source of power and the heating element and both being required to be on for activation of the heating element;
first and second processors, the first processor providing the first control signal to the first power switch along a first control path and one of the processors providing the second control signal to the second power switch along a second control path; and
a watchdog being in the first control path in electrical series between the first processor and the first power switch, the watchdog operable to normally gate the first control signal from the first processor to the first power switch and to monitor at least one of the processors, the watchdog further operable to interrupt the first control signal from the first processor to the first power switch so as to disable the heating element in response to the monitoring of the at least one processor, and the watchdog further operable to monitor the first processor and so disable the heating element in response to monitoring of the first processor, wherein the second control signal is not gated by the watchdog, and wherein the watchdog is further operable to interrupt the first signal and disable the heating element in response to a third control signal from the second processor to the watchdog.

14. A method of controlling a humidifier system having a heating element, first and second power switches in electrical series between a source of power and the heating element such that both switches are required to be on for activation of the heating element, first and second processors connected to, and operable to turn off, the switches upon the failure of any one of the processors, the method comprising:
sending a control signal to the first switch along a control path, the control signal originating at the first processor and gated by a watchdog in the control path between the first processor and the first switch;
monitoring at least one processor;
interrupting the gated control signal in order to disable the heating element in response to the monitoring of the at least one processor; and
sending a second control signal to the second switch along a second control path, the second control signal originating at the first processor and gated by the watchdog which is in the second control path between the first processor and the second switch.

15. A method of controlling a humidifier system having a heating element, first and second power switches in electrical series between a source of power and the heating element such that both switches are required to be on for activation of the heating element, first and second processors connected to, and operable to turn off, the switches upon the failure of any one of the processors, the method comprising:
sending a control signal to the first switch along a control path, the control signal originating at the first processor and gated by a watchdog in the control path between the first processor and the first switch;
monitoring at least one processor;
interrupting the gated control signal in order to disable the heating element in response to the monitoring of the at least one processor; and sending a second control signal to the second switch along a second control path, the second control signal originating at the second processor.

16. The method of claim 15 further comprising:

monitoring a timing signal from the first processor to the second processor;

monitoring a timing signal from the second processor to the first processor; and disabling all heating elements in response to a detected failure of one of the timing signals.

17. The method of claim 15, wherein the watchdog interrupts the gated control signal in response to receiving an override signal originating at the second processor.

* * * * *